United States Patent
Ben Muvhar

(10) Patent No.: US 10,702,368 B2
(45) Date of Patent: *Jul. 7, 2020

(54) GALLBLADDER IMPLANT AND SYSTEMS AND METHODS FOR THE DELIVERY THEREOF

(71) Applicant: LithiBlock Ltd., Peduel (IL)

(72) Inventor: Shmuel Ben Muvhar, Peduel (IL)

(73) Assignee: LithiBlock Ltd., Peduel (IL)

( * ) Notice: Subject to any disclaimer, the term of this patent is extended or adjusted under 35 U.S.C. 154(b) by 237 days.

This patent is subject to a terminal disclaimer.

(21) Appl. No.: 15/521,311

(22) PCT Filed: Oct. 27, 2015

(86) PCT No.: PCT/IL2015/051051
§ 371 (c)(1),
(2) Date: Apr. 24, 2017

(87) PCT Pub. No.: WO2016/067286
PCT Pub. Date: May 6, 2016

(65) Prior Publication Data
US 2017/0348086 A1 Dec. 7, 2017

Related U.S. Application Data

(60) Provisional application No. 62/069,164, filed on Oct. 27, 2014.

(51) Int. Cl.
*A61F 2/04* (2013.01)
*A61B 17/221* (2006.01)
(Continued)

(52) U.S. Cl.
CPC .............. *A61F 2/04* (2013.01); *A61B 17/221* (2013.01); *A61F 2/844* (2013.01); *A61F 2/848* (2013.01);
(Continued)

(58) Field of Classification Search
CPC ....................................................... A61F 2/04
(Continued)

(56) References Cited

U.S. PATENT DOCUMENTS 4,531,933 A 7/1985 Norton et al.
5,643,309 A 7/1997 Myler et al.
(Continued)

FOREIGN PATENT DOCUMENTS

CN 1863488 11/2006
CN 102670330 9/2012
(Continued)

OTHER PUBLICATIONS

International Search Report and the Written Opinion dated Jun. 19, 2017 From the International Searching Authority Re. Application No. PCT/IL2017/050384. (14 Pages).
(Continued)

*Primary Examiner* — Suzette J Gherbi

(57) ABSTRACT

A filter device for implantation in a gallbladder, comprising: a filter portion configured to filter gallstones of a certain minimum size to prevent them from exiting the gallbladder through an opening of the gallbladder; a blocking portion configured to push gallstones of a certain minimum size away from an opening of the gallbladder where the blocking portion is located distally from the filter portion with respect to the opening of the gallbladder; and, where the blocking portion and the filter portion do not attach to, or apply expansive radial force on, a wall of the gallbladder.

18 Claims, 6 Drawing Sheets

(51) Int. Cl.
*A61F 2/844* (2013.01)
*A61F 2/848* (2013.01)
*A61F 2/86* (2013.01)
*A61F 2/95* (2013.01)
*A61F 2/90* (2013.01)
*A61F 2/01* (2006.01)
*A61F 2/08* (2006.01)

(52) U.S. Cl.
CPC .................. *A61F 2/86* (2013.01); *A61F 2/90* (2013.01); *A61F 2/95* (2013.01); *A61B 2017/2212* (2013.01); *A61F 2/01* (2013.01); *A61F 2002/041* (2013.01); *A61F 2002/0817* (2013.01); *A61F 2002/8486* (2013.01)

(58) Field of Classification Search
USPC .................................. 623/23.64–23.65, 23.7
See application file for complete search history.

(56) References Cited

U.S. PATENT DOCUMENTS

| | | | |
|---|---|---|---|
| 5,925,062 | A | 7/1999 | Purdy |
| 6,093,199 | A | 7/2000 | Brown et al. |
| 6,342,059 | B1 | 1/2002 | Chevillon et al. |
| 6,432,134 | B1 | 8/2002 | Anson et al. |
| 6,616,680 | B1 | 9/2003 | Thielen |
| 6,623,507 | B2 | 9/2003 | Saleh |
| 7,524,319 | B2 | 4/2009 | Dubrul |
| 9,427,299 | B2 * | 8/2016 | Ben Muvhar ............. A61F 2/01 |
| 10,368,974 | B2 * | 8/2019 | Ben Muvhar ........... A61F 2/844 |
| 2002/0099437 | A1 | 7/2002 | Anson et al. |
| 2002/0193825 | A1 | 12/2002 | McGuckin, Jr. et al. |
| 2003/0040771 | A1 | 2/2003 | Hyodoh et al. |
| 2003/0057156 | A1 | 3/2003 | Peterson et al. |
| 2003/0078465 | A1 | 4/2003 | Pai et al. |
| 2003/0163204 | A1 | 8/2003 | Rix |
| 2004/0087997 | A1 | 5/2004 | Brenneman |
| 2004/0143209 | A1 | 7/2004 | Liu et al. |
| 2004/0193092 | A1 | 9/2004 | Deal |
| 2006/0036279 | A1 | 2/2006 | Eidenschink et al. |
| 2006/0074409 | A1 | 4/2006 | Schuermann |
| 2007/0027520 | A1 | 2/2007 | Sherburne |
| 2007/0083230 | A1 | 4/2007 | Javois |
| 2007/0112372 | A1 | 5/2007 | Sosnowski et al. |
| 2007/0239199 | A1 | 10/2007 | Jayaraman |
| 2008/0033457 | A1 | 2/2008 | Francischelli et al. |
| 2008/0140216 | A1 | 6/2008 | Ehrlinspiel et al. |
| 2008/0249636 | A1 | 10/2008 | Deal |
| 2008/0262592 | A1 | 10/2008 | Jordan et al. |
| 2009/0254172 | A1 | 10/2009 | Grewe |
| 2011/0230950 | A1 | 9/2011 | Knapp |
| 2012/0022550 | A1 * | 1/2012 | Ben Muvhar ............. A61F 2/01 606/127 |
| 2013/0144322 | A1 * | 6/2013 | Callaghan ................. A61F 2/01 606/191 |
| 2016/0242796 | A1 * | 8/2016 | Ben Muvhar ............. A61F 2/86 |
| 2016/0317167 | A1 | 11/2016 | Ben Muvhar |
| 2019/0099280 | A1 | 4/2019 | Ben Muvhar |
| 2019/0192272 | A1 * | 6/2019 | Ben Muvhar ............. A61F 2/86 |

FOREIGN PATENT DOCUMENTS

| | | |
|---|---|---|
| CN | 103068326 | 4/2013 |
| CN | 203424992 | 2/2014 |
| JP | 2005-508201 | 3/2005 |
| JP | 2005-534429 | 11/2005 |
| JP | 2012-521258 | 9/2012 |
| JP | 2013-537434 | 10/2013 |
| WO | WO 02/071977 | 9/2002 |
| WO | WO 2004/012587 | 2/2004 |
| WO | WO 2006/131930 | 12/2006 |
| WO | WO 2009/123715 | 10/2009 |
| WO | WO 2010/109467 | 9/2010 |
| WO | WO 2011/143137 | 11/2011 |
| WO | WO 2016/067286 | 5/2016 |
| WO | WO 2017/168418 | 10/2017 |
| WO | WO 2017/191645 | 11/2017 |

OTHER PUBLICATIONS

International Preliminary Report on Patentability dated Nov. 15, 2018 From the International Bureau of WIPO Re. Application No. PCT/IL2017/50499. (11 Pages).
Examiner-Initiated Interview Summary dated Mar. 14, 2019 From the US Patent and Trademark Office Re. U.S. Appl. No. 15/147,080. (3 pages).
Official Action dated May 25, 2018 From the US Patent and Trademark Office Re. U.S. Appl. No. 15/140,505. (35 Pages).
International Preliminary Report on Patentability dated May 11, 2017 From the International Bureau of WIPO Re. Application No. PCT/IL2015/051051. (8 Pages).
Office Action and Search Report dated Jun. 28, 2018 From the State Intellectual Property Office of the People's Republic of China Re. Application No. 201580071125.6 and Its Translation Into English.
International Preliminary Report on Patentability dated Oct. 11, 2018 From the International Bureau of WIPO Re. Application No. PCT/IL2017/050384. (9 Pages).
Communication Pursuant to Article 94(3) EPC dated Feb. 4, 2019 From the European Patent Office Re. Application No. 15808269.3. (4 Pages).
Official Action dated Dec. 13, 2015 From the US Patent and Trademark Office Re. U.S. Appl. No. 15/140,505. (0pages).
Invitation to Pay Additional Fees dated Aug. 17, 2017 From the International Searching Authority Re. Application No. PCT/IL2017/50499. (2 Pages).
International Search Report and the Written Opinion dated Oct. 20, 2017 From the International Searching Authority Re. Application No. PCT/IL2017/50499. (19 Pages).
Restriction Official Action dated Dec. 7, 2017 From the US Patent and Trademark Office Re. U.S. Appl. No. 15/147,080. (9 pages).
Official Action dated Dec. 5, 2018 From the US Patent and Trademark Office Re. U.S. Appl. No. 15/147,080. (17 pages).
Restriction Official Action dated Dec. 27, 2017 From the US Patent and Trademark Office Re. U.S. Appl. No. 15/140,505. (8 pages).
Official Action dated Apr. 23, 2018 From the US Patent and Trademark Office Re. U.S. Appl. No. 15/147,080. (36 pages).
Advisory Action Before the Filing of an Appeal Brief and Applicant-Initiated Interview Summary dated Jul. 15, 2015 From the US Patent and Trademark Office Re. U.S. Appl. No. 13/260,382.
Applicant-Initated Interview Summary dated May 27, 2015 From the US Patent and Trademark Office Re. U.S. Appl. No. 13/260,382.
Applicant-Initiated Interview Summary dated Feb. 10, 2016 From the US Patent and Trademark Office Re. U.S. Appl. No. 13/260,382.
Communication Pursuant to Article 94(3) EPC dated May 12, 2017 From the European Patent Office Re. Application No. 10719120.7. (4 Pages).
Communication Pursuant to Article 94(3) EPC dated Nov. 17, 2016 From the European Patent Office Re. Application No. 10719120.7. (6 Pages).
International Preliminary Report on Patentability dated Oct. 6, 2011 From the International Bureau of WIPO Re. Application No. PCT/IL2010/000258.
International Search Report and the Written Opinion dated Feb. 3, 2016 From the International Searching Authority Re. Application No. PCT/L2015/051051.
International Search Report and the Written Opinion dated Aug. 24, 2010 From the International Searching Authority Re. Application No. PCT/IL2010/000258.
Notice of Allowance dated Jun. 27, 2016 From the US Patent and Trademark Office Re. U.S. Appl. No. 13/260,382.
Notice of Reason for Rejection dated Nov. 29, 2013 From the Japanese Patent Office Re. Application No. 2012-501502 and Its Translation Into English.
Office Action dated Mar. 1, 2012 From the Israel Patent Office Re. Application No. 197800 and Its Translation Into English.

(56) References Cited

OTHER PUBLICATIONS

Official Action dated Mar. 3, 2015 From the US Patent and Trademark Office Re. U.S. Appl. No. 13/260,382.
Official Action dated Jun. 11, 2014 From the US Patent and Trademark Office Re. U.S. Appl. No. 13/260,382.
Official Action dated Sep. 11, 2013 From the US Patent and Trademark Office Re. U.S. Appl. No. 13/260,382.
Official Action dated Sep. 25, 2015 From the US Patent and Trademark Office Re. U.S. Appl. No. 13/260,382.
Official Action dated Feb. 26, 2013 From the US Patent and Trademark Office Re. U.S. Appl. No. 13/260,382.
Official Decision of Rejection dated Aug. 1, 2014 From the Japanese Patent Office Re. Application No. 2012-501502 and Its Translation Into English.
Restriction Official Action dated Dec. 6, 2012 From the US Patent and Trademark Office Re. U.S. Appl. No. 13/260,382.
Anderson et al. "7.9.1 Diameter; 7.9.4 Vessel Length", Iaizzo (Ed.), Handbook of Cardiac Anatomy, Physiology and Devices, 2nd Ed.(Chap.7): 117-118, 2010.
Elmunzer et al. "Percutaneous Cholecystostomy as a Bridge to Definitive Endoscopic Gallbaldder Stent Placement", Clinical Gastroenterology and Hepatology, 9: 18-20, 2011.
Itoi et al. "Endoscopic Gallbladder Drainage for Management of Acute Cholecystitis", Gastrointestinal Endoscopy, 71(6): 1038-1045, 2010.
Notice of Reason for Rejection dated Sep. 6, 2019 From the Japan Patent Office Re. Application No. 2017-542502 and Its Translation Into English. (12 Pages).
Supplementary European Search Report and the European Search Opinion dated Dec. 6, 2019 From the European Patent Office Re. Application No. 17792617.7. (10 Pages).

* cited by examiner

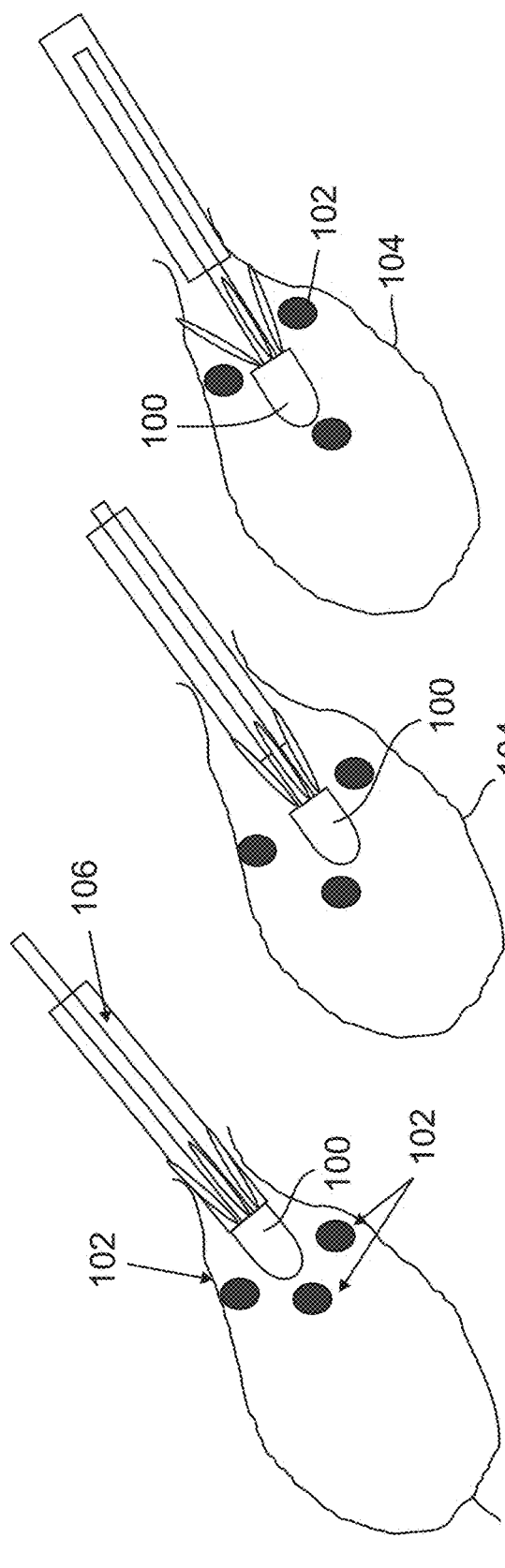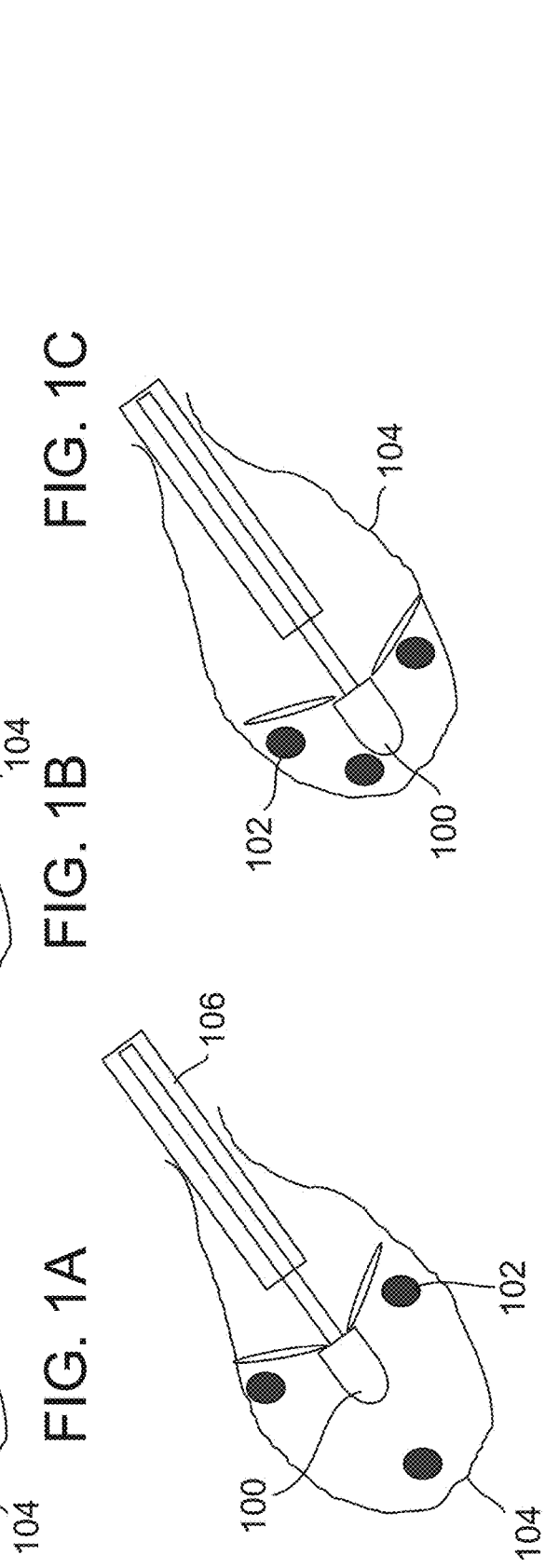

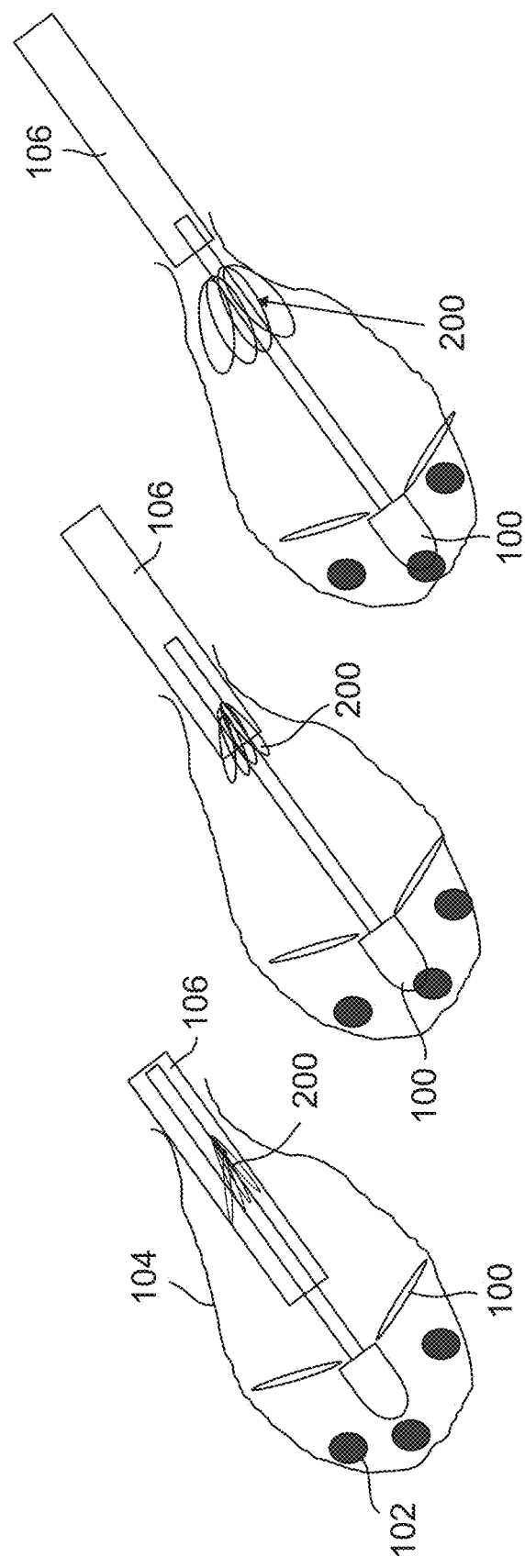

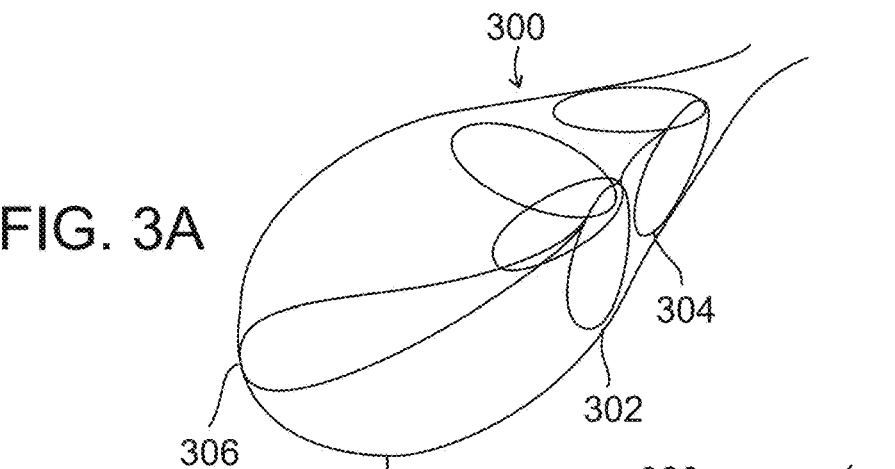
FIG. 3A
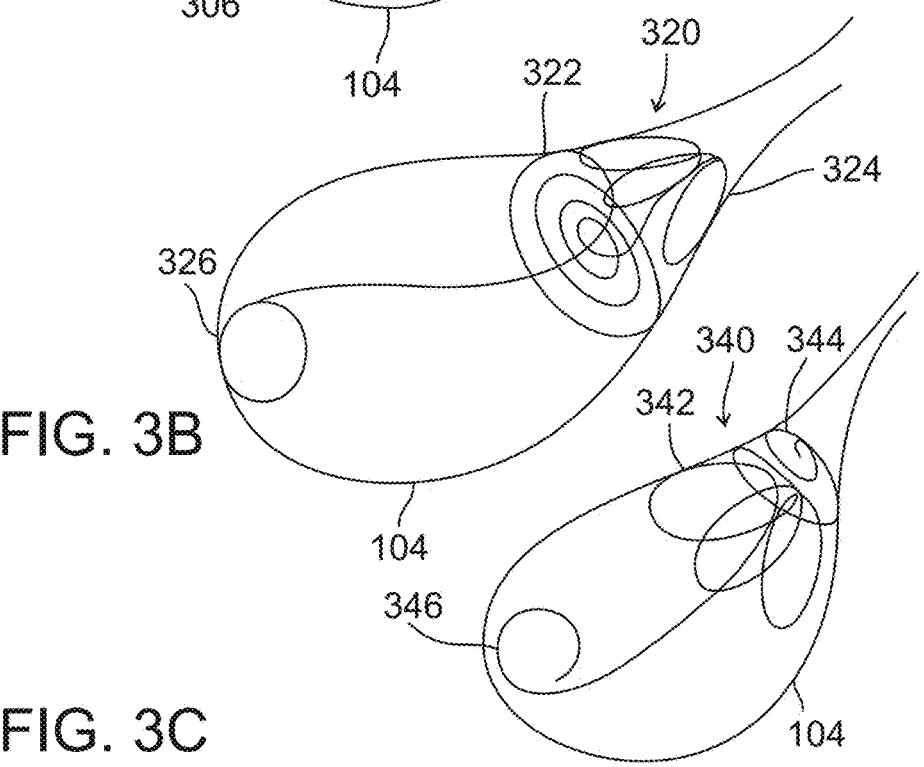
FIG. 3B
FIG. 3C
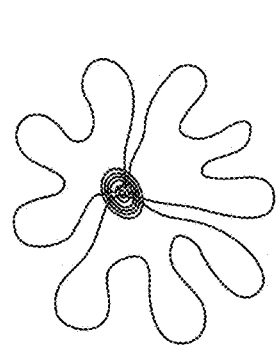
FIG. 4A
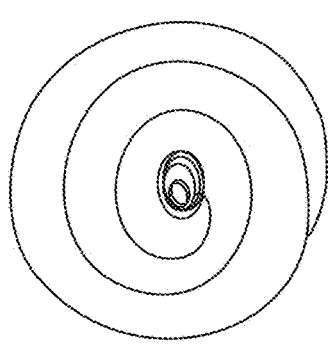
FIG. 4B
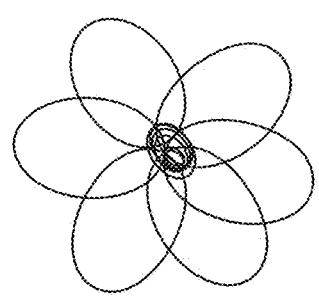
FIG. 4C

GALLBLADDER IMPLANT AND SYSTEMS AND METHODS FOR THE DELIVERY THEREOF

RELATED APPLICATIONS

This application is a National Phase of PCT Patent Application No. PCT/IL2015/051051 having International filing date of Oct. 27, 2015, which claims the benefit of priority under 35 USC § 119(e) of U.S. Provisional Patent Application No. 62/069,164, filed on Oct. 27, 2014. The contents of the above applications are all incorporated by reference as if fully set forth in their entirety.

PCT Patent Application No. PCT/IL2015/051051 is also related to U.S. patent application Ser. No. 13/260,382, filed on Sep. 26, 2011, now U.S. Pat. No. 9,427,299, the contents of which are incorporated by reference herein in their entirety.

FIELD AND BACKGROUND OF THE INVENTION

The present invention relates generally to treating medical conditions involving ducts and/or body lumens, for example by preventing occlusion of portions of the biliary tree during treatment device deployment.

"Stones" in the gallbladder and bile ducts are found in the entire population, some of them being asymptomatic, and some—symptomatic. In the U.S., 10-15% of the adult population (more than 20 million people) suffer from bile duct stones (about 20% of the population above 65 years of age suffer from gallstones), with more than two million new cases diagnosed annually, and more than 1,800,000 cholecystectomy procedures performed annually. Patients with gallstones are classified according to three groups: symptomatic, asymptomatic and those suffering from complications caused by the gallstones, such as cholecystitis, pancreatitis or obstructive jaundice.

SUMMARY OF THE INVENTION

There is provided in accordance with an exemplary embodiment of the invention, a filter device for implantation in a gallbladder, comprising: a filter portion configured to filter gallstones of a certain minimum size to prevent them from exiting the gallbladder through an opening of the gallbladder; a blocking portion configured to push gallstones of a certain minimum size away from an opening of the gall bladder where the blocking portion is located distally from the filter portion with respect to the opening of the gallbladder; and, where the blocking portion and the filter portion do not attach to, or apply expansive radial force on, a wall of the gallbladder.

In an embodiment of the invention, the blocking portion and the filter portion are the same.

In an embodiment of the invention, the device further comprises comprising an anchoring portion extending from the filter portion towards the opening of the gallbladder and configured to reduce movement of the filter device in the gallbladder.

In an embodiment of the invention, the device further comprises a stopper extending in the longitudinal axis of the filter device away from the opening of the gallbladder, where the stopper and the anchoring portion when taken together prevent migration of the anchoring portion away from the opening of the gall bladder.

In an embodiment of the invention, at least the filter portion is mesh.

In an embodiment of the invention, at least the filter portion is a coil.

In an embodiment of the invention, at least the filter portion is a perforated or porous sheet.

In an embodiment of the invention, the filter device is comprised of a single filament.

In an embodiment of the invention, the device is made from at least one of a metal, a shape memory alloy and a polymer.

In an embodiment of the invention, the device is adapted for eluting a pharmaceutical after implantation.

In an embodiment of the invention, the device is at least one of bioabsorbable and biodegradable.

In an embodiment of the invention, at least one of the blocking portion and filter portion are configured to prevent bio-film growth.

In an embodiment of the invention, at least one of the blocking portion, anchoring portion and filter portion are configured to prevent bio-film growth.

In an embodiment of the invention, the filter portion is configured to filter gallstones 5 mm or greater in diameter.

In an embodiment of the invention, the filter portion is configured with wires no more than 4 mm apart.

There is further provided in accordance with an exemplary embodiment of the invention, a system for delivery of a filter device for implantation in a gallbladder, comprising: a filter device including a blocking portion configured to push gall stones of a certain minimum size away from an opening of the gallbladder; and, a catheter configured for transit of the filter device therethrough to the gallbladder.

There is further provided in accordance with an exemplary embodiment of the invention, a method for implanting a filter device in a gallbladder, comprising: navigating the filter device to the gallbladder for implantation, the filter device including at least a blocking portion; entering the gall bladder at a gallbladder opening with the blocking portion; manually or automatically expanding the blocking portion in the gallbladder; pushing any gallstones in the gallbladder towards a distal end of the gallbladder and away from the gallbladder opening, thereby clearing a space within the gallbladder for proper and/or full expansion of the filter device; introducing a filter portion of the filter device to the gallbladder; and, manually or automatically expanding the filter portion in the gallbladder.

In an embodiment of the invention, the blocking portion and the filter portion are the same element, and blocking and filtering are performed simultaneously by the same element.

In an embodiment of the invention, the method further comprises deploying an anchoring portion after entering with the blocking portion and after introducing the filter portion.

In an embodiment of the invention, the method further comprises preventing the anchoring portion from moving away from the gall bladder opening using a stopper in conjunction with the anchoring portion.

In an embodiment of the invention, the method further comprises withdrawing the blocking portion after the filter portion has been expanded.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example, and not necessarily to scale, and are for purposes of illustrative discussion of embodiments of the invention. In this regard, the description taken with the drawings makes apparent to those skilled in the art how embodiments of the invention may be practiced.

In the drawings:

FIGS. 1A-1E are side views of a schematic deployment sequence of a blocking device, in accordance with an exemplary embodiment of the invention;

FIGS. 2A-2C are side views of a schematic deployment sequence of a filtering device after the blocking sequence shown in FIGS. 1A-1E has been performed, in accordance with an exemplary embodiment of the invention;

FIGS. 3A-3C are side views of two tier filtering devices, in accordance with exemplary embodiments of the invention;

FIGS. 4A-4C are top views of the filtering portion of filtering devices, in accordance with exemplary embodiments of the invention;

DESCRIPTION OF SPECIFIC EMBODIMENTS OF THE INVENTION

Figure 5A:
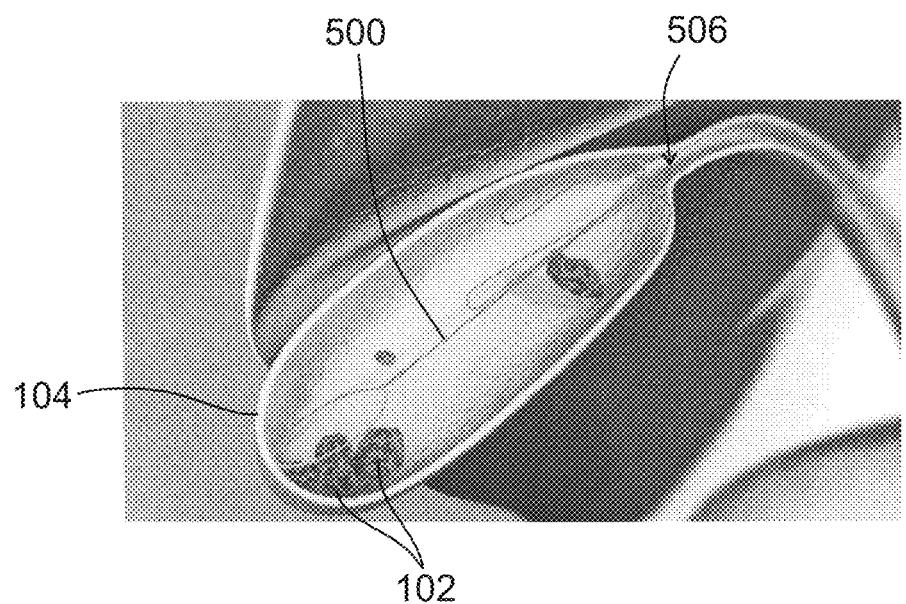
FIGS. 5A and 5B are perspective views of a filtering device, in accordance with an exemplary embodiment of the invention.

The present invention relates generally to treating medical conditions involving ducts and/or body lumens, for example by preventing occlusion of portions of the biliary tree during treatment device deployment.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Generally, systems, devices and methods for deploying filtering devices in a gallbladder are described. In some embodiments of the invention, a blocking device and/or a blocking portion of a device are used to push gall stones away from the opening to the gallbladder in order to make space for proper deployment of a gall stone filtering device. In some embodiments of the invention, the blocking device and the filter device are components of a system. In some embodiments of the invention, the blocking device is separate from the filtering device. In some embodiments of the invention, the blocking is performed by a filtering portion of the filtering device. In some embodiments of the invention, the filtering device is two-tiered. Optionally, one tier is configured to block and/or filter. Optionally, one tier is configured to anchor the device. In some embodiments of the invention, the device is provided with a stopper.

In an embodiment of the invention, the devices described herein spare the patient from suffering and/or surgery, and are intended to prevent the complications of cholecystectomy and anesthesia, operative mortality, postoperative infections (wound infection and other infections), and/or delayed impacts of gallbladder absence (impaired absorption, abdominal pain, etc.) by relieving and/or preventing the symptoms of cholecystitis, pancreatitis or obstructive jaundice, and/or preventing and/or delaying the need for cholecystectomy in patients with gallstones. In some embodiments of the invention, temporary relief, for example of pain induced by gallstones, is provided.

It should be understood that exemplary filter devices described herein are intended to prevent gallstones from passing from the gall bladder into the cystic duct while still allowing for normal bile flow and/or bodily fluids and/or secretions through the biliary tree and into the duodenum. In some exemplary embodiments of the invention, filtering is achieved without exerting potentially harmful levels of expansive radial force on the walls of the cystic duct and/or gall bladder. In some embodiments of the invention, no radial force is applied on the walls of the cystic duct and/or gallbladder.

FIGS. 1A-1E are side views of a schematic deployment sequence of a blocking device 100, in accordance with an exemplary embodiment of the invention. For efficiency, description of device embodiments of the invention (FIGS. 1A-1E and FIGS. 2A-2C) are described in conjunction with the methods of their deployment, in conjunction with FIG. 7.

Figure 7:
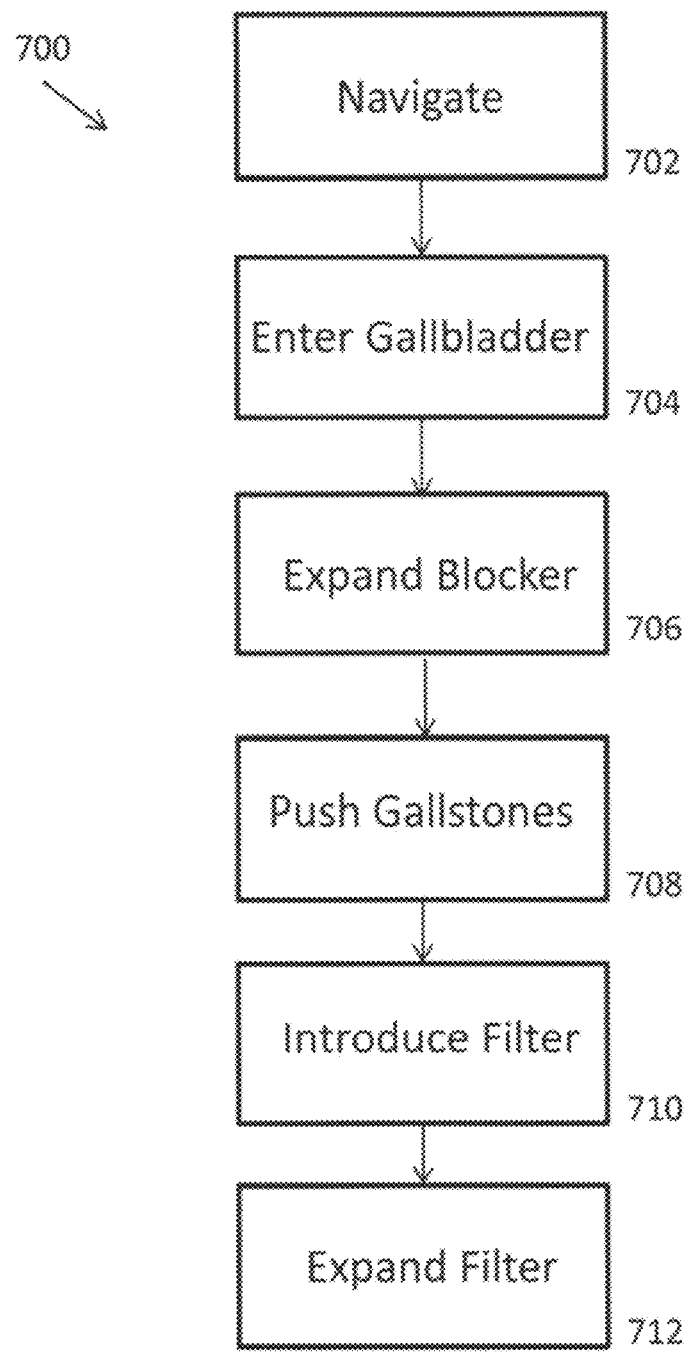
FIG. 7 is a flowchart of a method of deploying a filtering device in a gall bladder, in accordance with an exemplary embodiment of the invention.

FIG. 7 is a flowchart 700 depicting a method of implanting a filter device 200 in the gallbladder 104, in accordance with an embodiment of the invention. In an embodiment of the invention, implantation may be performed without general anesthesia and is considered to be minimally invasive. In an embodiment of the invention, the filter device 200 and/or the blocking device 100 are inserted and/or navigated (702) into the GI tract via the mouth, through to the esophagus, through to the stomach and then into the duodenum. Navigation and/or insertion are accomplished using an endoscope and/or a guiding wire and/or an elongated tool, such as a catheter 106, as chosen by the attending medical professional performing the procedure, in an embodiment of the invention.

The filter device 200 is advanced the Sphincter of Oddi/papila into the common bile duct, in an exemplary embodiment of the invention. A sphincterotomy of the Sphincter of Oddi is performed, if required and/or desired, similarly to the method commonly used in endoscopy and ERCP. The filter device 200 is implanted at a desired implantation site by navigating the filter device 200 from the common bile duct through to the cystic duct and/or the gallbladder 104. Contrast material in used order to image the gallbladder 104 and/or the cystic duct and/or the gastro-intestinal tract, in some exemplary embodiments of the invention. Optionally, other commonly available imaging techniques are used for the implantation, for example X-ray and/or ultrasound.

In an exemplary embodiment of the invention, the filter device 200 and/or the blocking device 100 are inserted and/or navigated (702) into the patient in a contracted form. In some embodiments of the invention, the blocking device 100 precedes the filter device 200 such that during implanting, the blocking device 100 enters (704) the gall bladder 104 first (shown in FIGS. 1A-1B), radially expands (706) in the gall bladder 104 (shown in FIGS. 1C-1D) and pushes (708) any gallstones 102 in the gallbladder 104 down to or at least towards a distal end of the gallbladder 104 and away from the gallbladder opening (shown in FIGS. 1D-1E), thereby clearing a space within the gall bladder for proper and/or full expansion of the filter device.

In an embodiment of the invention, the filter device 200 is then introduced (710) to the gallbladder 104 (now that the area in the gallbladder 104 near the opening has been cleared or substantially cleared of gallstones 102) so that the filter device 200 can properly expand (712) to provide filtering. Introduction of the filter device 200 and expansion in a cleared area is schematically shown in FIGS. 2A-2C. In some embodiments of the invention, the filter device 200 expands (712) to its intended size and shape upon arrival at the desired site of implantation.

In some embodiments of the invention, the filter device 200 is also provided with blocking capability and functionally operates to both block (to clear out gall stones to make room for filter expansion) and filter. Exemplary devices for performing both functions in the same device are shown and described with respect to FIGS. 3A-3C and FIGS. 4A-4C, below. In some embodiments of the invention, the blocking device 100 also functions as a filter, in addition to and/or alternatively to the filtering device 200.

In some embodiments of the invention, the filter device 200 expands (712) as a consequence of its own spring-like behavior, for example upon deployment from a catheter 106 which was used to pass the filter device 200 to the cystic duct and/or gallbladder 104, the device 200 springs into designed shape and size once the catheter 106 is no longer holding the filter device 200 in a contracted state. Optionally, the filter device 200 expands (712) as a result of its shape memory characteristic. In some embodiments of the invention, an expansion balloon is used to expand the filter device 200. Due to the special anatomic structure of the cystic duct in the gallbladder region, more than one balloon and/or one balloon inflation may be used, for example, using a flexible balloon for initial inflation and a rigid and/or a semi-rigid balloon for filter device fixation.

Optionally, the blocking device 100 is withdrawn after the filter device 200 has been deployed, for example through an opening in the filter device configured for passage of the blocking device 100 therethrough.

Besides the implantation method described above, any other technique leading to the Sphincter of Oddi and/or the gallbladder 104, such as laparoscopy or open surgery, may be used.

In an embodiment of the invention, the filter device 200 and/or the blocking device 100 can be removed or are designed to be bio-absorbed at any time.

In some embodiments of the invention, medical imaging is used for guiding the navigation of the biliary tree and/or implantation of the blocking device 100 and/or filter device 200 at the correct implantation site. Optionally, a scope is used to provide imaging. Optionally, x-ray is used to provide imaging. Optionally, ultrasound is used to provide imaging.

FIGS. 3A-3C are side views of two tier filtering devices 300, 320, 340, respectively, in accordance with exemplary embodiments of the invention. In an embodiment of the invention, the two tier filtering devices 300, 320, 340 are provided with a combination filter/blocker portion 302, 322, 342, respectively and an anchoring portion 304, 324, 344, respectively.

In an embodiment of the invention, the filter/blocker portion 302, 322, 342 is configured to enter the gall bladder 104 prior to the second tier, or anchoring portion 304, 324, 344, which when the filter/blocker portion 302, 322, 342 expands pushes any gallstones away from the opening of the gall bladder 104, both to prevent gall stones from entering the biliary tree and also to ensure proper deployment/expansion of the anchoring portion 304, 324, 344.

In an embodiment of the invention, the anchoring portion does not exert radial force on the wall of the gallbladder 104 and/or does not anchor by attaching itself or latching onto a wall of the gallbladder 104. In some embodiments of the invention, the anchor portion 304, 324, 344 works in combination with a stopper 306, 326, 346 which when taken together stretch substantially the length of the gallbladder 104, preventing the devices 302, 320, 340 from moving axially in the gallbladder (that is, preventing the device from migrating away from the opening to gallbladder).

FIGS. 4A-4C are top views of the filter/blocking portions 302, 322, 342 of filtering devices 300, 320, 340, in accordance with exemplary embodiments of the invention. In some embodiments of the invention, at least the filter/blocking portion 302, 322, 342 is configured so that there is spacing between the wires sufficient for blocking gallstones of a specified minimum size, but are also far enough apart to avoid growth of bacterial films, and other bio-film growth, between the wires which could block the natural flow of material from the gallbladder into the biliary tree.

In some embodiments of the invention, the filter/blocking portion is configured to block gallstones approximately 5 mm or more in diameter. In some embodiments of the invention, spaces between wires form an opening no greater than 4 mm×4 mm.

In some embodiments of the invention, the filter portion and/or blocking portion and/or anchoring portion are mesh, spiral/coiled and/or a perforated sheet. In some embodiments of the invention, the device is shaped to allow for slight movement within the implantation site in order to prevent or delay bio-film growth via device motion. Optionally, the device is moved by movement of the gallbladder and/or the surroundings of the implantation site itself. In an embodiment of the invention, the device moves and/or flexes to cause any accumulation of bio-film to break, crack and/or at the very least create openings through the bio-film such that natural secretions of the gall bladder continue to flow.

The device material is selected to be biocompatible and/or bio-absorbable, in an exemplary embodiment of the invention. Optionally, the device is constructed of a polymer material. In some embodiments of the invention, the device is at least partly metal. Optionally, the device is at least a shape memory alloy such as nickel titanium, also known as Nitinol®. In some embodiments of the invention, at least a portion of the device is coated, for example with Teflon® or other similarly inert or highly non-reactive coating. Optionally, at least a portion of the device and/or the coating is adapted to elute a substance, for example a pharmaceutical. Optionally, an anti-bio-film agent, like an antibiotic, is eluted from and/or covers at least a portion of the device.

In some embodiments of the invention, the entire device is constructed of a single filament. In an embodiment of the invention, the blocking portion (if separate, such as in the case of the device shown in FIGS. 1A-1E) and/or the filter portion and/or anchoring portion are separately formed elements which are connected together. In some embodiments of the invention, at least two of the portions are connected by at least a single filament. Optionally, at least two of the sections are connected by a plurality of filaments.

Optionally, the anchoring portion 304, 324, 344 could have a configuration shown in any of FIGS. 4A-4C. Optionally, a separate blocking or filter portion could have a configuration shown in any of FIGS. 4A-4C.

Figure 5B:
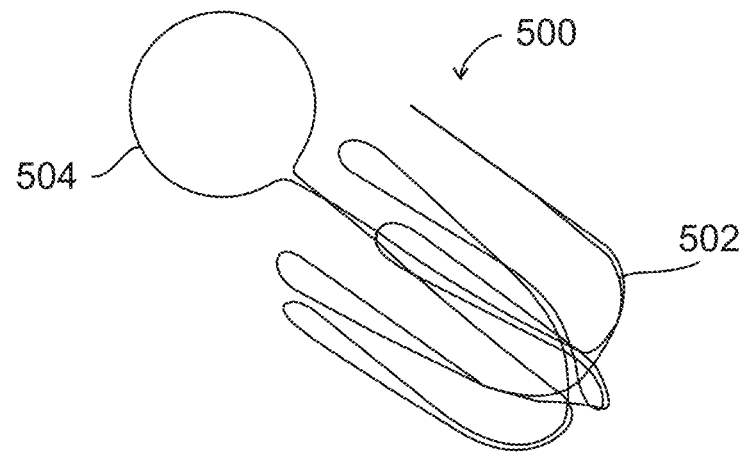

FIGS. 5A and 5B are perspective views of a filtering device 500, in accordance with an exemplary embodiment of the invention. FIG. 5B shows an exemplary filtering device 500 configured with a filter/blocking portion 502 and a stopper 504. FIG. 5A is a perspective view of a cross-sectioned gallbladder 104 with the filtering device 500 implanted within the gallbladder 104. In an embodiment of the invention, filtering device 500 is deployed after a blocking device 100 has been deployed. Optionally, the blocking device 100 is removed after the filtering device 500 has been placed in the gallbladder 104. In some embodiments of the invention, the filter/blocking portion 502 is located near an opening 506 to the gallbladder 104 to prevent gallstones 102 of a certain minimum size from leaving the gallbladder 104. In some embodiments of the invention, the stopper 504 is configured to avoid puncturing a wall of the gallbladder, for example by having a rounded shape. In some embodiments of the invention, the stopper 504 (including the length of filament leading to the stopper) and the filter/blocking portion 502 operate in conjunction (by substantially stretching the length of the gallbladder) to reduce the chance of movement of the filter/blocking portion 502 from migrating away from the opening 506.

Figure 6:
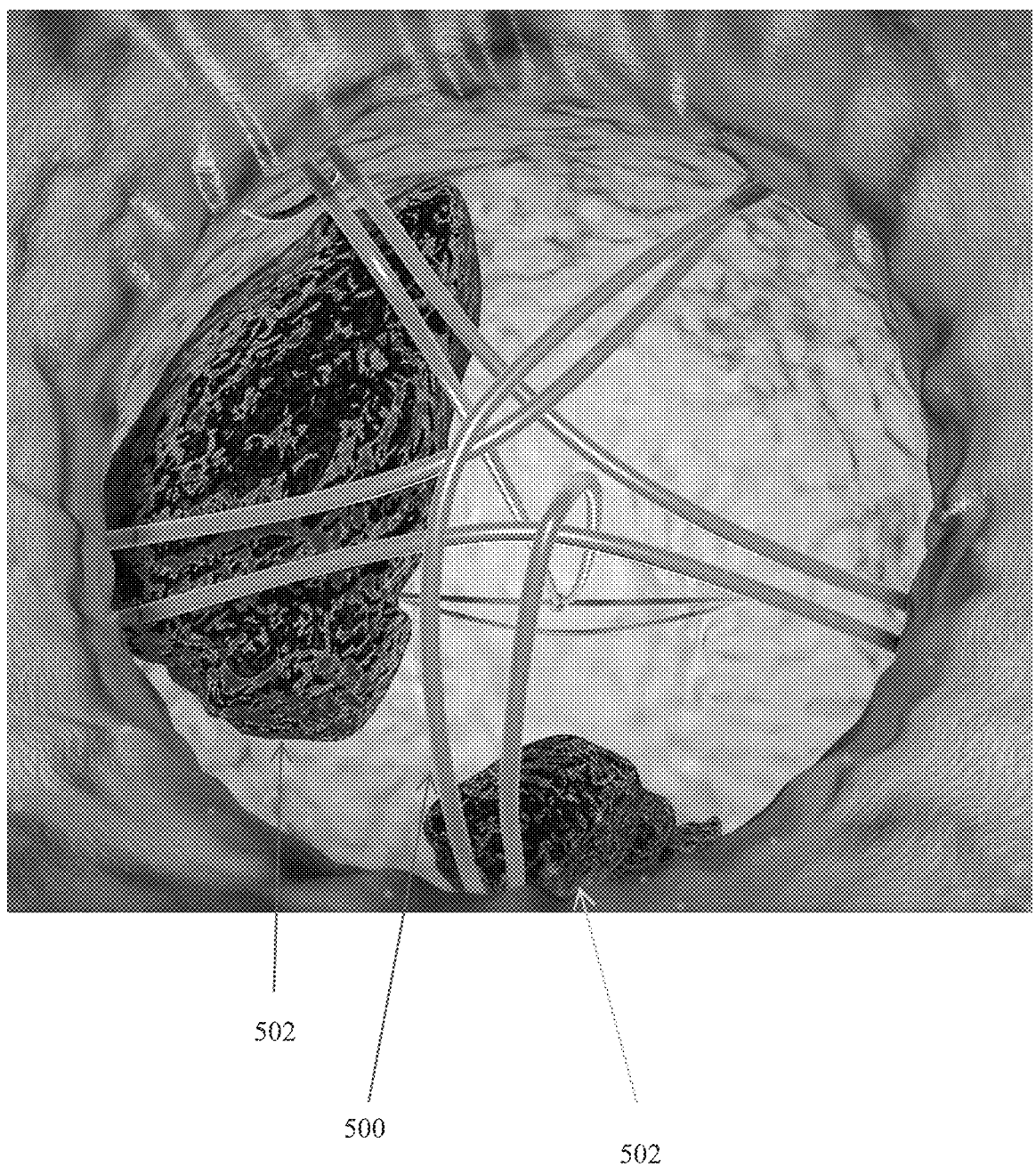
FIG. 6 is a top view of a filtering device in situ, in accordance with an exemplary embodiment of the invention.

FIG. 6 is a top view of a filtering device 600 in situ, in accordance with an exemplary embodiment of the invention. In an embodiment of the invention, the device 600 is blocking/filtering gall stones 602 of a specified minimum size and preventing them from leaving the gallbladder.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Further, described ranges are intended to include numbers outside any range described within statistical error and/or inherent measurement equipment limitations.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for implanting a filter device in a gallbladder, comprising:
navigating the filter device to the gallbladder for implantation, the filter device including at least a blocking portion;
entering the gall bladder at a gallbladder opening with the blocking portion;
manually or automatically expanding the blocking portion in the gallbladder;
pushing any gallstones in the gallbladder towards a distal end of the gallbladder and away from the gallbladder opening, thereby clearing a space within the gallbladder for proper and/or full expansion of the filter device;
introducing a filter portion of the filter device to the gallbladder; and,
manually or automatically expanding the filter portion in the gallbladder.

2. The method according to claim 1, where the blocking portion and the filter portion are the same element, and blocking and filtering are performed simultaneously by the same element.

3. The method according to claim 1, further comprising deploying an anchoring portion after entering with the blocking portion and after introducing the filter portion.

4. The method according to claim 3, further comprising preventing the anchoring portion from moving away from the gall bladder opening using a stopper in conjunction with the anchoring portion.

5. The method according to claim 1, further comprising withdrawing the blocking portion after the filter portion has been expanded.

6. The method according to claim 1, wherein the blocking portion and the filter portion do not attach to, or apply expansive radial force on, a wall of the gallbladder during expanding.

7. The method according to claim 1, further comprising anchoring the filter device in the gallbladder using an anchoring portion extending from the filter portion towards the opening of the gallbladder a.

8. The method according to claim 7, further comprising using a stopper extending in the longitudinal axis of the filter device away from the opening of the gallbladder in addition to the anchoring portion, to prevent migration of the anchoring portion away from the opening of the gall bladder.

9. The method according to claim 1, wherein the introducing of the filter portion is of a mesh.

10. The method according to claim 1, wherein the introducing of the filter portion is of a coil.

11. The method according to claim 1, wherein the introducing of the filter portion is of a perforated or porous sheet.

12. The method according to claim 1, wherein the filter device is comprised of a single filament.

13. The method according to claim 1, wherein the device is made from at least one of a metal, a shape memory alloy and a polymer.

14. The method according to claim 1, further comprising eluting a pharmaceutical after implantation from the device.

15. The method according to claim 1, further comprising at least one of bioabsorbing and biodegrading the device after implantation.

16. The method according to claim 1, further comprising configuring the at least one of the blocking portion and filter portion to prevent bio-film growth on.

17. The method according to claim 1, wherein filtering is of gallstones 5 mm or greater in diameter.

18. The method according to claim 1, further comprising configuring the filter portion with wires no more than 4 mm apart.

* * * * *